United States Patent
Glas et al.

(10) Patent No.: US 8,349,386 B2
(45) Date of Patent: Jan. 8, 2013

(54) FUNCTIONAL SERUM PROTEIN PRODUCT FOR USE IN INFANT FOOD AND THERAPEUTIC COMPOSITIONS AND METHODS FOR THE PREPARATION THEREOF

(75) Inventors: Cornelis Glas, Tietjerk (NL); Rob Te Biesebeke, Amersfoort (NL); Jantje Kromkamp, Ede (NL); Gijsbertus Klarenbeek, Ommen (NL)

(73) Assignee: Friesland Brands B.V., Meppel (NL)

( * ) Notice: Subject to any disclaimer, the term of this patent is extended or adjusted under 35 U.S.C. 154(b) by 0 days.

(21) Appl. No.: 13/185,353

(22) Filed: Jul. 18, 2011

(65) Prior Publication Data
US 2011/0281012 A1    Nov. 17, 2011

Related U.S. Application Data

(63) Continuation of application No. 12/595,042, filed as application No. PCT/NL2008/050212 on Apr. 16, 2008, now abandoned.

(30) Foreign Application Priority Data

Apr. 16, 2007  (NL) ..................................... 1033698

(51) Int. Cl.
A23C 9/154  (2006.01)
C07K 1/00  (2006.01)
(52) U.S. Cl. ........................................ 426/580; 530/350
(58) Field of Classification Search ................. 530/350; 426/580
See application file for complete search history.

(56) References Cited

U.S. PATENT DOCUMENTS 5,169,666 A    12/1992    Woychik

FOREIGN PATENT DOCUMENTS

| EP | 1 133 238 | 7/2004 |
|----|-----------|--------|
| EP | 1 673 975 | 6/2006 |
| FR | 2 592 769 | 7/1987 |
| NL | 1023239 | 10/2004 |
| NL | 1025900 | 11/2004 |
| WO | WO-94/13148 | 6/1994 |
| WO | WO-96/08155 | 3/1996 |
| WO | WO-2004/112508 | 12/2004 |

OTHER PUBLICATIONS

International Search Report for PCT/NL2008/050212, mailed on Jul. 11, 2008, 6 pages.
International Preliminary Report on Patentability for PCT/NL2008/050212, issued on Oct. 20, 2009, 9 pages.
Lawrence et al., Desalination (2006) 200:305-306.
Maubois, Australian Journal of Dairy Technology (1991) 46(2):91-95.
Van Hekken and Holsinger, Le Lait (2000) 80:69-76.

*Primary Examiner* — Maryam Monshipouri
(74) *Attorney, Agent, or Firm* — Morrison & Foerster LLP

(57) ABSTRACT

The invention relates to a serum protein product, suitable as an ingredient for foods and therapeutic compositions, in particular infant and baby foods. The invention also provides a method for the preparation of the serum protein product, based on micro filtration of milk. The invention provides a method for the preparation of a serum protein product, comprising the preparation of a permeate through micro filtration of cow's milk at a temperature of between 10 and 20° C. utilizing a membrane having a pore size of between 0.3 and 0.5 μm.

10 Claims, 1 Drawing Sheet

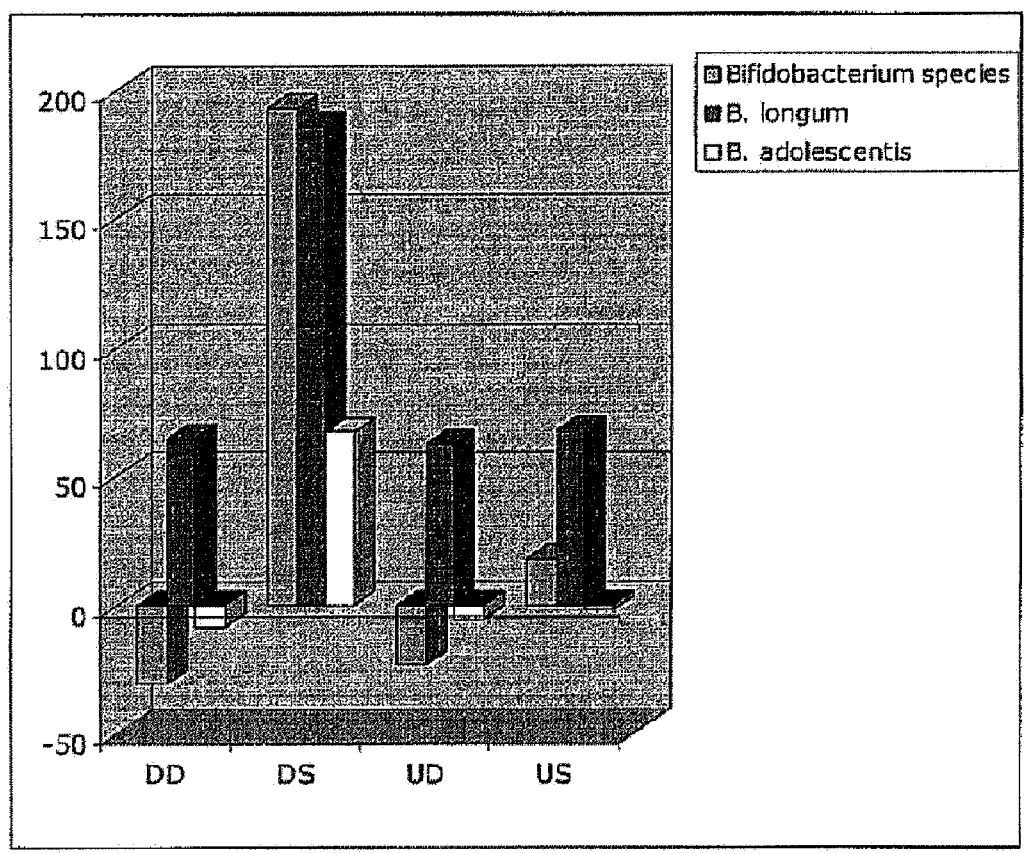

FUNCTIONAL SERUM PROTEIN PRODUCT FOR USE IN INFANT FOOD AND THERAPEUTIC COMPOSITIONS AND METHODS FOR THE PREPARATION THEREOF

CROSS-REFERENCE TO RELATED APPLICATIONS

This application is a continuation of U.S. application Ser. No. 12/595,042 having an international filing date of 16 Apr. 2008, now abandoned, which is the national phase of PCT application PCT/NL2008/050212 having an international filing date of 16 Apr. 2008, which claims benefit of Netherlands application No. 1033698 filed 16 Apr. 2007. The contents of the above patent applications are incorporated by reference herein in their entirety.

The invention relates to a serum protein product, suitable as an ingredient for foods and therapeutic compositions, in particular infant and baby foods. The invention further provides a method for the preparation of the serum protein product, based on microfiltration of milk from ruminants, and the use thereof in foods and therapeutic compositions.

If human milk is insufficiently available, or if food with human milk is not possible or desirable for other reasons, infant food based on cow's milk is generally regarded as a good alternative. Because cow's milk and human milk are significantly different in composition, in particular protein composition, already a great deal of research has been carried out to make the composition of infant food approximate that of human milk as best as possible. This process is also referred to as humanizing cow's milk. The starting point is then that the specific composition of human milk brings with it the desired dietary functionalities for the child.

As for the dietary functionality of human milk, ever more knowledge is available. A recent development in this field has brought to light the importance of a proper availability of the amino acid proline, via nutrition, for the intestinal wall maturation after birth, or for prevention and treatment of undue or undesired permeability of the intestinal wall, or for a proper closure of the tight junctions, respectively. This is described inter alia in NL-1023239, NL-1025900 and NL-1027262. Proline serves as a precursor for the formation of polyamines, which are synthesized in the body with ornithine as intermediate. In addition to proline, also glutamate and arginine are needed for this formation. Polyamines subsequently have the above-mentioned positive effects on the intestinal wall. These effects are of importance not only to children, but also to ill adults.

In addition, reference may be made to WO 01/58283 which addresses the importance of a proper supply of glutamate and/or a precursor for glutamate for the treatment or prevention of hyperpermeability or undesired permeability of the intestinal wall. WO 01/58283 also indicates the importance of the availability of polyamines and/or precursors for polyamines, such as proline. Further, J. Nutr. Biochem. 15, 2004, 442-451 describes that in prematurely born children the synthesis of intestinal citrulline and arginine is still limited, with a deficiency of polyamines as one of the possible consequences. It follows that a proper proline supply is also of importance to prematures.

In the infant foods of NL-1023239, NL-1025900 and NL-1027262 a sufficiently high proline level is achieved by enriching a cow's milk protein fraction that is rich in whey proteins, with proline in free amino acid form. Especially for infant food, however, it is of importance that the desired composition be achieved as much as possible on the basis of milk components, hence without adding components foreign to milk. In addition, it is an important endeavor to arrange not only for the amino acid composition but also for the protein composition of the infant food to resemble that of human milk as much as possible. This implies that proline (and possibly other amino acids) should preferably be present in an infant food not as free amino acid but in the form of protein.

The object of the present invention is to provide a milk protein product that is suitable as a protein source in a food or therapeutic composition. In particular, the object of the invention is to provide a milk protein product allowing an infant or baby food to be prepared which approximates the dietary functionality, such as the amino acid and protein composition, of human milk as closely as possible. Furthermore, the object of the invention is to provide a method which makes the preparation of such a milk protein product on an industrial scale attractive.

Surprisingly, it has been found that the above-mentioned objectives can be achieved by the use of a method in which milk is microfiltered with a membrane having a pore size of between 0.3 and 0.5 μm and at a temperature of between 10 and 20° C. A milk protein product obtainable according to a method of the present invention is formed by the microfiltration permeate, which, as to protein composition, consists of serum proteins (>60%) and casein proteins (<40%) and of which the casein proteins comprise at least 75% of β-casein. This concerns a proline-rich serum protein product through the presence of the proline-rich β-casein. The proline content of the product according to the present invention is 5 to 15 g of proline per 100 g of protein, preferably 6 to 11 g per 100 g, and is thus comparable to the content of human milk. This allows dispensing with the addition of proline to infant food in free amino acid form and as a component foreign to milk. In addition, in this way, the wish to make the protein composition of infant food more similar to that of human milk, is met better.

Accordingly, the invention provides a method for the preparation of a serum protein product, comprising the preparation of a permeate through microfiltering of cow's milk with a membrane having a pore size of between 0.3 and 0.5 μm, at a temperature of between 10 and 20° C. The use of microfiltration to separate casein and serum proteins in milk from each other is known per se, and so is the use of the microfiltration permeate, after further processing, in infant food. EP-1133238 describes for instance the recovery of serum proteins from milk through microfiltration of milk in a conventional crossflow microfiltration installation at a temperature of 50-55° C.

Microfiltration in a method of the present invention, by contrast, is carried out at a temperature of between 10 and 20° C. It has been found that such a temperature range is particularly suitable for the isolation of beta casein in the permeate. Moreover, it does not require any special and/or costly measures, such as far-reaching cooling or heating, to practice the process on an industrial scale. Microfiltration temperatures lower than 10° C. or higher than 20° C. have the drawback of being difficult to realize on a large scale and of being relatively expensive. In a specific aspect, microfiltration is done at a temperature of 10 to 15° C., as at 10 to 12° C.

A method according to the invention is not known from the prior art. U.S. Pat. No. 5,169,666 discloses microfiltration of milk at a lower temperature (2-8° C.) and utilizing a smaller pore size (0.1 or 0.2 μm). WO 96/08115 concerns the separation of serum and whey proteins from skim milk through microfiltration and ultrafiltration. As in U.S. Pat. No. 5,169,666, a preference is expressed for membranes having a relatively small pore size, viz. 0.07-0.2 μm. The temperature is typically between 5 and 60° C. and preferably between 10 and 50° C. All Examples of WO 96/08115 concern microfiltration at 50° C. with a pore size of 0.1 or 0.2 µm. WO 94/13148 describes microfiltration of raw milk utilizing a ceramic membrane having a pore size of approximately 0.1 µm at a temperature of between 40 and 50° C., in order to obtain a serum albumin content of 10% or higher.

As starting material, milk from ruminants can be used, such as cow's milk, goat milk, camel milk, donkey milk, buffalo milk, sheep milk, horse milk or lama milk. Typically, cow's milk is used, preferably the low-fat fraction of the raw milk (called skim milk). This can be prepared according to a standard method, for instance by centrifuging raw milk, followed by thermizing to lower the initial germ count of the milk.

For the microfiltration, any conventional apparatus for crossflow microfiltration can be used. Thus, for instance, use can be made of a spiral-wound microfiltration membrane, for instance as described in EP-A-1673975. Preferably, a process system with multiple spiral-wound modules is used. It has been found that it is helpful that in the crossflow microfiltration process measures are taken for reducing the transmembrane pressure across the membrane, in such a manner that the transmembrane pressure is 2.5 bar at a maximum. For that reason, preferably, the transmembrane pressure during microfiltration in a method according to the invention is kept relatively low, that is, 2.5 bar at a maximum. Good results as regards the protein composition of the permeate have for instance been obtained at a maximum transmembrane pressure of 2 bars. The average transmembrane pressure may vary, and is for instance 1.5 or 1.3 bar. In a specific embodiment, the maximum transmembrane pressure is 1 bar, as 0.9 bar.

Instead of reducing the transmembrane pressure, a different solution may be the use of microfiltration membranes having a gradient in the porosity or thickness of the membrane layer.

In a method according to the invention, standard microfiltration membranes having a pore size of between 0.3 and 0.5 µm may be used. As is known in general, pore size influences the eventual protein composition of the permeate and the retentate. In the light of the present invention, the pore size proves to have an influence inter alia on both the serum protein to casein ratio and the proportion of beta casein in the casein fraction. In an embodiment, use is made of a membrane, for instance a spiral-wound membrane, having a pore size of between 0.3 and 0.5 µm, preferably between 0.3 and 0.45 µm.

In a specific embodiment, the invention provides a method for the preparation of a serum protein product, comprising the preparation of a permeate through microfiltering of skim milk with a membrane having a pore size of between 0.3 and 0.5 µm, at a temperature of between 10 and 20° C., for instance 10-14° C., while the transmembrane pressure during microfiltration is 2.5 bar at a maximum, preferably 2 bar at a maximum.

In another specific embodiment, the invention provides a method for the preparation of a serum protein product, comprising the preparation of a permeate through microfiltering of (cow's) milk with a membrane having a pore size of 0.3 µm, at a temperature of between 10 and 20° C., preferably 10-15° C., while the transmembrane pressure during microfiltration is 2.5 bar at a maximum, preferably 2 bar at a maximum.

In another specific embodiment, the invention provides a method for the preparation of a serum protein product, comprising the preparation of a permeate through microfiltering of (cow's) milk with a membrane having a pore size of 0.45 µm, at a temperature of between 10 and 20° C., preferably 10-15° C.

After carrying out the microfiltration step, the microfiltration permeate may be further treated according to one or more conventional processes, such as ultrafiltration, nanofiltration, ion exchange, electrodialysis, reverse osmosis, desalination, evaporation and spray drying. For instance, Na and K are removed.

A further aspect of the invention concerns providing a serum protein product obtainable according to the method of the invention. Depending on the microfiltration conditions (for instance pore size, temperature, transmembrane pressure), the ratio of serum protein to casein and/or the content of proline-rich beta casein can vary. The invention provides for instance a serum protein product containing at least 60% of serum protein and at most 40% of casein, and wherein the casein fraction comprises at least 75%, preferably at least 80%, of beta casein. The serum protein product according to the present invention finds application in baby and infant food and therapeutic compositions. Normally, a serum protein to casein ratio of approximately 60:40 is contemplated in infant food to bring the protein composition in line with human milk as best as possible. In the use of the serum protein product according to the present invention, this can be achieved by using, in addition to the serum protein product, a casein source such as skim milk, caseinate, acid casein or milk protein concentrate prepared through ultra- or microfiltration. A specific advantage of the serum protein product according to the invention is that the choice of the casein source is free for the producer and hence may depend, for instance, on availability at the respective location and time. Also in connection with this, the serum protein product according to the present invention preferably contains 65% of serum protein at a minimum and 35% of casein at a maximum. The minimum content of casein may vary. Preferably, the serum protein product contains at least 10%, more preferably at least 12 or 15% of casein. In a specific aspect, the invention provides a product having at least 25% of casein, for instance 28, 30, 32, 33 or 35% of casein. In view of the proline content of beta casein, it is preferred that in particular a relatively low casein content is coupled with a relatively high proportion of beta casein, preferably more than 75%, as 76, 77, 78% or more. Representative products according to the present invention therefore contain 10-40%, 10-35%, 15-40%, 15-38% or 15-38% of casein, of which the beta casein content is 75% or higher, preferably higher than 75%. Utilizing a method of the invention, a very high content of beta casein within the casein fraction can be achieved. It provides, for instance, a serum protein concentrate having a casein content of 5.5% and a serum protein content of 33.4% (resulting in a protein composition with 86% of serum protein and 14% of casein), wherein the casein fraction comprises 95% of beta casein and in addition 5% of alpha casein. Another example concerns a serum protein product comprising 68% of serum protein and 32% of casein, of which 79% of beta casein.

As mentioned earlier, a serum protein product according to the invention has a number of important features as regards the functional nutritional value. In particular, it approximates the protein composition of human milk on different points. For instance, the proline content of a serum protein product is between 5 and 15 grams of proline per 100 g of protein, preferably 6 to 11 grams of proline per 100 g of protein. In contrast to known (ingredients for) (infant) foods with such contents of proline, the proline is present not as free amino acid but, just as in human milk, as part of a polypeptide from milk. Supplementation with proline in the form of free amino acids is therefore not necessary. The invention accordingly provides a serum protein product in which the proline is substantially present as part of a polypeptide. In this way, the wish to make the protein composition of infant food more similar to that of human milk is met.

Another development considered of interest in the field of humanizing cow's milk concerns the amino acid threonine. The presence of a relatively high content of threonine in infant food is mostly linked to the presence of glycomacropeptide (GMP), as appears inter alia from J. Ped. Gastr. Nutr. 32, 2001, 127-130. GMP is a cleavage product of x-casein, which is formed during cheese-making under the influence of the enzyme chymosin. Consequently, it occurs in sweet whey, which is often used as a whey protein source for infant food. The oligopeptide GMP is rich in threonine, which upon overdosing can cause hyperthreoninemia in prematures.

There are a number of solutions known to prevent an unduly high loading with threonine. This concerns the lowering of the threonine content of the cow's milk products. Use of acid whey instead of sweet whey is a known solution., as is clear from inter alia J. Ped. Gastr. Nutr. 32, 2001, 127-130. Acid whey contains no GMP because in the production of acid whey no enzymatic curdling of the milk occurs. Another known solution concerns the removal of GMP from sweet whey before using this in infant food. This is known from EP-1048226. A third known solution concerns using, instead of sweet whey, a serum protein product based on microfiltration permeate of milk. This is described in EP-1133238. There, too, no enzymatic curdling of the milk has been carried out in the production of the respective serum protein product, which results in a product having a relatively low content of threonine.

A serum protein product according to the present invention usually has a threonine content of between 4.7 and 6 grams per 100 grams of protein, with the threonine, just as in human milk, being present in intact protein molecules. Without wishing to be bound to any theory, the present inventors propose that what is relevant for the threonine loading of children is not so much the threonine content as the form in which the threonine is present. It appears from J. Dairy Sci. 75, 1992, 1380-1388 that GMP can already be absorbed by the small intestine in intact form, that is, without further hydrolysis. This rapid absorption of GMP possibly has negative consequences for the synthesis of mucin in the intestine, for which threonine is an important amino acid source. This would argue in favor of the availability of threonine in a form less quick to be absorbed, so that the availability of threonine in the intestine is better. Also in human milk, threonine occurs in intact protein molecules. The fact that threonine in a serum protein product according to the invention is substantially present in the form of intact protein molecules, instead of in oligopeptides or as free amino acids, could contribute to this. The product according to the invention contains for instance between 4.7 and 6 g of threonine per 100 grams of protein, without involving too high a threonine loading. The serum protein product according to the present invention may therefore be said to involve a "slow release threonine" content, comparable to that of human milk.

Yet another favorable nutritional property of a serum protein product obtainable through microfiltration according to the invention is that it contains a relatively high content of freely available (ionic) calcium (usually circa 600-700 mg per 100 g of protein). As a result, already upon minor heating of the product, a maximum denaturation of especially whey proteins may be achieved. See for instance EP-311795. The result is a product that can be optimally employed for preventing allergy to proteins and/or a product that has a tolerance-enhancing effect, partly owing to the promotion of an optimum closure of the tight junctions mentioned earlier.

A further aspect of the invention concerns a method for the preparation of food or therapeutic composition, preferably a baby or infant food, utilizing at least the serum protein product according to the present invention. The method usually comprises the standard steps of mixing at least one protein-, lipid- and carbohydrate-source, optionally supplemented with minerals, oligo components and other ingredients. Also, a food or therapeutic composition, preferably a baby or infant food, is provided which is obtainable according to such a method. In comparison with the hitherto most current cow's milk protein sources based on whey protein and casein, as used in the preparation of human milk replacements, the milk proteins in a serum protein product according to the invention are not, or hardly so, associated. This provides the advantage, among others, that on the basis of this protein source in combination with the usual fats, a highly stable and fine emulsion can be formed. With this, the digestion of the end product can be improved, and/or the occurrence of digestive disorders be prevented.

In the (baby and infant) food and therapeutic compositions according to the present invention, it is also possible that, in addition to the serum protein product, they contain other proteins such as whey proteins, α-lactalbumin, lactoferrin and vegetable proteins, as from soybean or wheat. In an embodiment, the method concerns the preparation of a baby or infant food, preferably with a serum protein to casein ratio of approximately 60:40 by weight. Eligible for use as an additional protein source are skim milk, caseinate, acid casein or milk protein concentrate. Moreover, both the serum protein product and other proteins can have undergone a hydrolysis step. This is for instance conventional for preventing allergies whereby protein is hydrolyzed under the influence of pancreas enzymes.

It is further conventional to add to baby and infant food and therapeutic compositions carbohydrates, such as lactose and oligosaccharides, lipids and ingredients such as vitamins, amino acids, minerals, taurine, carnitine, nucleotides and polyamines, and antioxidants such as BHT, ascorbyl palmitate, vitamin E, α- and β-carotene, lutein, zeaxanthin, lycopene and lecithin. The lipids are mostly of vegetable origin. In addition, the food or the therapeutic composition may be enriched with polyunsaturated fatty acids, such as gamma-linolenic acid, dihomo-gamma-linolenic acid, arachidonic acid, stearidonic acid, eicosapentaenoic acid, docosahexaenoic acid and docosapentaenoic acid. With a view to a proper development of the intestinal flora, probiotics may be added, such as lactobacilli and/or bifidobacteria, as well as prebiotics. A preferred combination of probiotics is for instance *Bifidobacterium lactis* with *L. casei, L. paracasei, L. salivarius* or *L. reuter*. Examples of prebiotics include fuco-, fructo- and/or galacto-oligosaccharides, both short- and long-chain, (fuco)sialyloligosaccharides, branched (oligo)saccharides, sialic acid-rich milk products or derivatives thereof, inulin, carob bean flour, gums, which may or may not be hydrolyzed, fibers, protein hydrolysates, nucleotides, etc.

A food or therapeutic composition according to the invention can be advantageously used to promote the maturation of the intestinal wall and/or a proper closure of the tight junctions. It has also been found that it can stimulate the mucus formation of the intestinal wall and/or promote the colonization resistance of the intestinal flora. The invention thus provides a resistance-enhancing protein concentrate. Without wishing to be bound to any theory, the present inventors propose that while threonine is an important amino acid source for an optimum synthesis of mucin, it is in particular the peptides resulting from enzymatic digestion of beta casein that promote mucus secretion. This means that a serum protein product enriched in beta casein according to the invention with a threonine content of 4.7-6 g/100 g not only does not have any disadvantages (since it is present as "slow release threonine") but also can contribute to an optimum mucus formation at the level of the intestinal wall. This can involve both the induction and the preservation of mucus formation. A serum protein product according to the invention can therefore, through stimulated mucus formation, have a favorable influence on the build-up of resistance to pathogens.

What is more, it has been found that a serum protein product according to the invention has a specifically favorable effect on the intestinal flora in comparison with traditionally applied whey proteins from sweet whey. For more details, see Example 4 below.

The invention will now be illustrated in and by the following Examples.

EXAMPLE 1

COMPARATIVE EXAMPLE

Skim milk was prepared by centrifuging raw milk and then thermizing the skim milk for 15 s at 67° C. This skim milk was microfiltered in a process system with 1 spiral-wound module (DSS, pore size 0.15 µm, membrane surface 14 m$^2$), at a temperature of 10° C. and a maximum transmembrane pressure of 1.8 bar (on average 1.3 bar). The skim milk was filtered batchwise to a volume reduction factor (VRF) of 3.3. The permeate was then concentrated by means of ultrafiltration (UF) and dried to a powdery serum protein concentrate. The casein content of the serum protein concentrate was 5.5% and the serum protein content was 33.4%, resulting in a protein composition with 86% of serum protein and 14% of casein. The casein fraction was comprised of 95% of β-casein and in addition 5% of α-casein.

The serum protein fraction comprised 24% of α-la and 75% of β-lg. The amino acid composition is represented in Table 1.

TABLE 1

| Amino acid | Content (g/100 g of crude protein) |
|---|---|
| Arginine | 2.5 |
| Cysteine | 2.9 |
| Histidine | 2.3 |
| Isoleucine | 5.7 |
| Leucine | 12.9 |
| Lysine | 9.9 |
| Methionine | 2.2 |
| Phenylalanine | 4.0 |
| Threonine | 5.2 |
| Tryptophan | 2.4 |
| Tyrosine | 3.3 |
| Valine | 5.8 |
| Aspartic acid | 12.3 |
| Glutamic acid | 19.5 |
| Serine | 4.8 |
| Proline | 5.6 |
| Glycine | 2.1 |
| Alanine | 4.2 |

EXAMPLE 2

Skim milk was prepared by centrifuging raw milk and then thermizing the skim milk for 15 s at 76° C. This skim milk was microfiltered in a process system with four spiral-wound modules (DSS, pore size 0.45 µm, membrane surface 56 m$^2$), at a temperature of 10° C. and a maximum transmembrane pressure of 2.5 bar (on average 1.5 bar). The skim milk was filtered to a VRF of 3.3 in a continuous process mode. The permeate was then concentrated by means of UF and dried, so that a powdery serum protein concentrate was obtained. The casein content of the serum protein concentrate was 15.9% and the serum protein content was 33.4%, resulting in a protein fraction with 68% of serum protein and 32% of casein. The casein fraction was comprised of 79% of β-casein and in addition 18% of α-casein and 3% of κ- and γ-casein. The serum protein fraction comprised 25% of α-la and 73% of β-lg and 1% of BSA. The amino acid composition is represented in Table 2.

TABLE 2

| Amino acid | Content (g/100 g of crude protein) |
|---|---|
| Arginine | 2.4 |
| Cysteine | 2.3 |
| Histidine | 2.1 |
| Isoleucine | 4.8 |
| Leucine | 11.8 |
| Lysine | 9.1 |
| Methionine | 2.1 |
| Phenylalanine | 4.0 |
| Threonine | 4.8 |
| Tryptophan | 2.0 |
| Tyrosine | 3.5 |
| Valine | 5.2 |
| Aspartic acid | 10.6 |
| Glutamic acid | 18.0 |
| Serine | 4.9 |
| Proline | 6.4 |
| Glycine | 2.0 |
| Alanine | 4.1 |

EXAMPLE 3

Prepared was a food for infants, which was composed as specified in Table 3 below, starting from the serum protein concentrate of Example 1. The serum protein concentrate contained 5.6% of proline and 5.2% of threonine and the Na caseinate 10.5% of proline and 4.9% of threonine, expressed as a percentage of the total crude protein.

TABLE 3

| Component | | per 100 g |
|---|---|---|
| Proteins | g | 10.7 |
| Serum protein concentrate | g | 7.1 |
| casein | g | 3.6 |
| Proline (% of crude protein) | % | 7.1 |
| Threonine (% of crude protein) | % | 5.1 |
| Fat | g | 27 |
| Linoleic acid | g | 3.3 |
| α-Linolenic acid | g | 0.47 |
| DHA | mg | 53 |
| AA | mg | 53 |
| Carbohydrates | g | 55 |
| Lactose | g | 53 |
| Maltodextrin | g | 2 |
| Dietary fiber | g | 1.8 |
| Galacto-oligosaccharides | g | 1.8 |
| Minerals, Vitamins | | |
| Nucleotides | g | 1.9 |

EXAMPLE 4

This Example illustrates the favorable effect on the intestinal flora of a serum protein product according to the invention (herein called SPC) in comparison with DEMINAL90, a conventional whey protein product based on sweet whey.

A serum protein product obtainable according to a method of the invention utilizing a 0.45 μm membrane and DEMINAL90 were incorporated into media that served as nutrient source in pH-controlled batch cultures (BATCH 2 and BATCH 3, respectively). In addition, the two products were incorporated in two separate media after being treated with proteases. These media were also used as nutrient source in pH-controlled batch cultures (BATCH 4 and BATCH 5, respectively). The proteases had been so selected and so incubated with the protein products as to simulate the conditions in the gastrointestinal part of the human body as best as possible, that is, pepsin treatment at pH 3.0 and a treatment with a pancreas extract at pH 6.5. The medium contained yeast extract, $NaHCO_3$, $KH_2PO_4$, $K_2HPO_4$, NaCl, cysteine.HCl, $MgSO_4$, $CaCl_2$, hemin, Resazurin, Tween-80 and vitamin K.

The sterile, pH-controlled batch culture with medium was made anaerobic and inoculated with freshly obtained baby feces of a healthy child, the feces having been incorporated in a slurry based on PBS. The different protein sources were added to the batch cultures. Also, a reference culture with a minimal amount of protein and without additional test protein sources (BATCH 1) was prepared which was also inoculated with feces slurry.

The batch culture was incubated for 6 hours at a temperature of 37° C., after which samples were taken which were analyzed for the presence of microbial organisms. The analysis was carried out by means of DNA amplification and a DNA hybridization assay. The assay was set up and validated for detection and quantification of both *Bifidobacterium* genera, *Lactobacillus* genera and other bacterial species, such as *Escherichia coli, Clostridium difficile, Salmonella, Bifidobacterium longum, Lactobacillus casei*. The hybridization was carried out with fluorescent probes specific to the bacterial species. Specifically bound probes were quantified with a dedicated scanner. The measured fluorescence signal was correlated with the amounts of bacteria by means of software. The signals were corrected for the background signal obtained from BATCH 1.

The corrected signals of the tested batches that correspond to Bifidobacteria are shown in FIG. 1. The following codes were used:
DD=digested DEMINAL90
DS=digested serum protein product of the invention
UD=undigested DEMINAL90
US=undigested serum protein product of the invention The y-axis plots the number of bacteria in arbitrary units that correspond to the fluorescence measured after hybridization and standardization for each bacterial species.

The figure shows the stimulating effect of a digested serum protein product according to the invention in comparison with a conventional whey protein preparation. The expectation is that this favorable effect can be ascribed at least for a part to the presence of beta casein.

EXAMPLE 5

This Example describes four different examples (A, B, C and D) of a method according to the invention for the preparation of a serum protein isolate.
A) Skim milk was prepared by centrifuging raw milk and then thermizing the skim milk for 15 s at 67° C. This skim milk was microfiltered in a process system with two spiral-wound modules (Parker, pore size 0.3 μm, membrane surface 28 m², at a temperature of 15° C. and a maximum transmembrane pressure of 0.9 bar (on average 0.6 bar). The skim milk was filtered to a VRF of 4.0 in a continuous process mode. The casein content of the serum protein isolate was 0.8% based on total dry matter and the serum protein content was 6.7% of serum protein based on total dry matter, resulting in a protein fraction with 89% of serum protein and 11% of casein.
B) Skim milk was prepared by centrifuging raw milk and then thermizing the skim milk for 15 s at 67° C. This skim milk was microfiltered in a process system with two spiral-wound modules (Parker, pore size 0.3 μm, membrane surface 28 m²), at a temperature of 10° C. and a maximum transmembrane pressure of 0.9 bar (on average 0.6 bar). The skim milk was filtered to a VRF of 4.0 in a continuous process mode. The casein content of the serum protein isolate was 1.3% based on total dry matter and the serum protein content was 7.3% of serum protein based on total dry matter, resulting in a protein fraction with 85% of serum protein and 15% of casein.
C) Skim milk was prepared by centrifuging raw milk and then thermizing the skim milk for 15 s at 67° C. This skim milk was microfiltered in a process system with two spiral-wound modules (DSS, pore size 0.45 μm, membrane surface 28 m²), at a temperature of 10° C. and a maximum transmembrane pressure of 0.9 bar (on average 0.6 bar). The skim milk was filtrated to a VRF of 2.0 in a continuous process mode. The casein content of the serum protein isolate was 2.6% based on total dry matter and the serum protein content was 6.3% serum protein based on total dry matter, resulting in a protein fraction with 70% of serum protein and 30% of casein.
D) Skim milk was prepared by centrifuging raw milk and then thermizing the skim milk for 15 s at 67° C. This skim milk was microfiltered in a process system with two spiral-wound modules (DSS, pore size 0.45 μm, membrane surface 28 m²), at a temperature of 10° C. and a maximum transmembrane pressure of 2.5 bar (on average 1.5 bar). The skim milk was filtrated to a VRF of 2.0 in a continuous process mode. The casein content of the serum protein isolate was 1.5% based on total dry matter and the serum protein content was 3.0% of serum protein based on total dry matter, resulting in a protein fraction with 67% of serum protein and 33% of casein.

The invention claimed is:

1. A serum protein product, containing 15-38% casein, wherein the casein fraction comprises more than 75% of beta casein.

2. The serum protein product of claim 1, wherein said protein contains 6 to 11 grams of proline per 100 g of protein.

3. The serum protein product of claim 1, wherein said protein contains more than 4.7 grams of threonine per 100 g of protein.

4. The serum protein product of claim 1, wherein the freely available calcium content is at least 600 mg per 100 g of protein.

5. The serum protein product of claim 1 which is obtainable by a method comprising microfiltering milk from a ruminant with a microfiltration membrane having a pore size of between 0.3 and 0.5 μm, at a temperature of between 10 and 20° C. to obtain a permeate.

6. The product of claim 5, wherein the temperature is 10 to 15° C.

7. The product of claim 5, wherein the transmembrane pressure during said microfiltering is a maximum of 2.5 bar.

8. The product of claim 5, wherein the microfiltration membrane is spiral-wound.

9. The product of claim 5, wherein the pore size of the microfiltration membrane is approximately 0.45 μm.

10. The product of claim 5, wherein the method further comprises treating the permeate with one or more of the following processes: ultrafiltration, nanofiltration, ion exchange, electrodialysis, reverse osmosis, desalination, evaporation and spray-drying.

* * * * *